United States Patent
Mroczkowski et al.

(10) Patent No.: US 10,292,718 B2
(45) Date of Patent: May 21, 2019

(54) GRAPHENE-ENHANCED ORTHOPEDIC CUTTING INSTRUMENTS

(71) Applicant: Greatbatch Ltd., Clarence, NY (US)

(72) Inventors: Matthew L. Mroczkowski, Fort Wayne, IN (US); Lasantha Viyannalage, Pittsford, NY (US); Steven W Winn, Lancaster, NY (US)

(73) Assignee: VIANT AS&O HOLDINGS, LLC, Tempe, AZ (US)

( * ) Notice: Subject to any disclaimer, the term of this patent is extended or adjusted under 35 U.S.C. 154(b) by 296 days.

(21) Appl. No.: 15/201,835

(22) Filed: Jul. 5, 2016

(65) Prior Publication Data
US 2017/0000502 A1    Jan. 5, 2017

Related U.S. Application Data

(60) Provisional application No. 62/188,126, filed on Jul. 2, 2015.

(51) Int. Cl.
*A61B 17/16* (2006.01)
*A61B 18/00* (2006.01)

(52) U.S. Cl.
CPC ............ *A61B 17/1666* (2013.01); *A61B 2018/00095* (2013.01)

(58) Field of Classification Search
CPC ................................................ A61B 17/1666
See application file for complete search history.

(56) References Cited

U.S. PATENT DOCUMENTS

| | | | |
|---|---|---|---|
| 3,633,583 A | 1/1972 | Fishbein | |
| 4,023,572 A * | 5/1977 | Weigand | A61B 17/1666 30/276 |
| 4,811,632 A * | 3/1989 | Salyer | A61B 17/1666 76/115 |
| 5,049,165 A * | 9/1991 | Tselesin | B24D 3/06 51/295 |

(Continued)

FOREIGN PATENT DOCUMENTS

| | | |
|---|---|---|
| EP | 1226785 | 7/2002 |
| FR | 2903591 | 1/2008 |

(Continued)

OTHER PUBLICATIONS

Extended European Search Report, Application 16177576.2, dated Oct. 27, 2016.

*Primary Examiner* — Nicholas W Woodall
(74) *Attorney, Agent, or Firm* — Grossman, Tucker, Perreault & Pfleger, PLLC

(57) ABSTRACT

An orthopedic reamer cutting tool is disclosed that incorporates a second material such as graphene having an increased coefficient of thermal conductivity to remove heat generated at the tissue cutting surface during use. The reamer is constructed having a hemispherical cutting shell that extends from an equatorial base to an apex at a distal end. A plurality of cutting teeth, each having a tissue cutting surface, extend from the exterior of the cutting shell. A reamer driver interface may be positioned spanning the diameter of the reamer base. The second material, having increased thermal conductivity, may be applied to the interior and/or exterior shell surfaces. In addition, the second material may be incorporated within the shell or the driver interface.

18 Claims, 3 Drawing Sheets

(56) References Cited

U.S. PATENT DOCUMENTS

| | | | |
|---|---|---|---|
| 5,488,774 A | 2/1996 | Janowski | |
| 6,364,662 B1 * | 4/2002 | Kumar | A61C 8/0089 433/165 |
| 7,498,089 B2 * | 3/2009 | Omori | C23C 30/005 428/336 |
| 2006/0195110 A1 | 8/2006 | White et al. | |
| 2011/0300505 A1 | 12/2011 | Jessop et al. | |
| 2012/0271357 A1 | 10/2012 | Arthur et al. | |
| 2013/0204254 A1 | 8/2013 | Slone et al. | |
| 2014/0173995 A1 * | 6/2014 | Bailey | E21B 10/00 51/295 |
| 2015/0005887 A1 | 1/2015 | Dimitrakopoulos et al. | |

FOREIGN PATENT DOCUMENTS

| | | |
|---|---|---|
| JP | S55137803 | 10/1980 |
| JP | 2012071370 | 4/2012 |
| JP | 2013222918 | 10/2013 |
| KR | 2013-0040367 | 4/2013 |
| SU | 1000254 | 2/1983 |
| WO | 90/07908 | 7/1990 |

\* cited by examiner

GRAPHENE-ENHANCED ORTHOPEDIC CUTTING INSTRUMENTS

CROSS REFERENCE TO RELATED APPLICATION

This application claims priority from U.S. Provisional Application Ser. No. 62/188,126, filed Jul. 2, 2015.

TECHNICAL FIELD

The present invention relates to the art of orthopedic cutting devices, more particularly, to a reamer device designed to remove tissue from the acetabulum.

BACKGROUND OF THE INVENTION

Reamers are devices intended to remove tissue and bone from the human body. Specifically, the reamer of the present invention is designed to remove tissue from the cotyloid cavity of the acetabulum in preparation for the insertion of a hip joint supported by a prosthetic cup seated in the cavity.

In general, acetabular reamers are constructed with a continuous partially hemispherical surface. This partial hemispherical structure is ideally suited to create a cavity in which to fit a prosthetic cup. Prosthetic cups generally have a curved exterior surface that is inserted into the cotyloid cavity.

A series of discrete tissue cutting openings are typically positioned throughout the outer partially hemispherical surface and extend through the reamer wall thickness. These tissue cutting openings are characteristically designed such that the specific surface that cuts the tissue is provided within the perimeter of the opening.

Many problems are associated with these traditional reamer designs such as prior art reamer designs found in U.S. Pat. Nos. 7,217,272, 6,001,105, and 5,299,893 to Salyer as well as U.S. Pat. No. 6,951,563 to Wolford. One is that prior art reamers tend to generate heat as they cut bone and tissue during an orthopedic surgical procedure. In some cases, these reamers are connected to motors that rotate the attached reamer at speeds in excess of 1,000 RPM. In addition, a significant amount of torque is generated against the reamer as it is applied to bone and tissue. As a result, heat is generated at the cutting site as the reamer is used. This heat may cause necrosis of bone and tissue that is adjacent to the reamer. Furthermore, such heat generation may cause the cutting surface of the reamer to become damaged.

Prior art reamers are typically composed of stainless steel, which is not an efficient conductor of heat. Stainless steel has a relatively low coefficient of thermal conductivity of about 16 $W \cdot m^{-1} \cdot K^{-1}$. As a result, heat that is generated during use of a stainless steel reamer, typically becomes concentrated at the tissue cutting edge. The present invention, therefore, provides a reamer cutting device that is at least partially constructed with a material having increased thermal conductivity properties, more preferably, a material with an increased coefficient of thermal conductivity that removes heat from the tissue cutting surface.

The reamer of the present invention is thus designed to divert heat away from the cutting surface, thus minimizing heat generation during use thereby, reducing the possibility of causing tissue necrosis, patient trauma, and potential reamer structural damage. Heat that is generated during use of the reamer is removed from the cutting surface that is in physical contact with bone and tissue.

SUMMARY OF THE INVENTION

The present invention is an orthopedic reamer designed to cut and remove tissue and bone material. The device is designed to efficiently remove tissue and bone to thereby create a cavity for the insertion of an orthopedic implant. Specifically, the present invention is directed to a reamer that is preferably designed to remove tissue and bone from the acetabulum.

The reamer of the present invention comprises a reamer assembly that connects to a reamer shaft. The reamer assembly further comprises a partially hemispherical shell composed of a first material with a rotational axis that extends through a hemispherical sidewall extending from the apex to an equatorial rim that circumferentially extends about the axis. The hemispherical sidewall is constructed with a plurality of openings that extend through a shell thickness. Each of the openings having a raised portion that forms a tissue cutting surface.

In an embodiment, a second material having a thermal conductivity that is greater than that of the first material of the shell, such as graphene having a coefficient of thermal conductivity of between 3,000 to 5,000 $W \cdot m^{-1} \cdot K^{-1}$, is incorporated with the reamer of the present invention. This second material is designed to act as a heat sink to divert heat away from the tissue at the cutting surface. Thus, an advantage of the cutting tool of the present invention is the capability to reduce heat from the cutting surfaces of the reamer as the reamer cuts through bone and tissue. As defined herein, thermal conductivity is a measure of the ability of a material to allow the flow of heat from its warmer surface through the material to its colder surface. Thermal conductivity is determined as the heat energy transferred per unit of time and per unit of surface area divided by the temperature gradient, which is the temperature difference divided by the distance between the two surfaces (the thickness of the material), expressed in watts per meter per kelvin.

In a preferred embodiment, at least a layer of the second material having the increased thermal conductivity, such as graphene, is applied to an interior or exterior surface of the hemispherical dome. In addition, the second material may also be incorporated within the sidewall of the dome cutting shell or incorporated within a driver interface at the base of the dome. This second material having an increased thermal conductivity is designed to conduct heat away from the cutting surface to thus minimize heat generation at the cutting site during use. Additional materials other than graphene may be used as the second material. In a preferred embodiment, the second material has a coefficient of thermal conductivity that is greater than 16 $W \cdot m^{-1} \cdot K^{-1}$.

DETAILED DESCRIPTION OF THE PREFERRED EMBODIMENT

Figure 1:
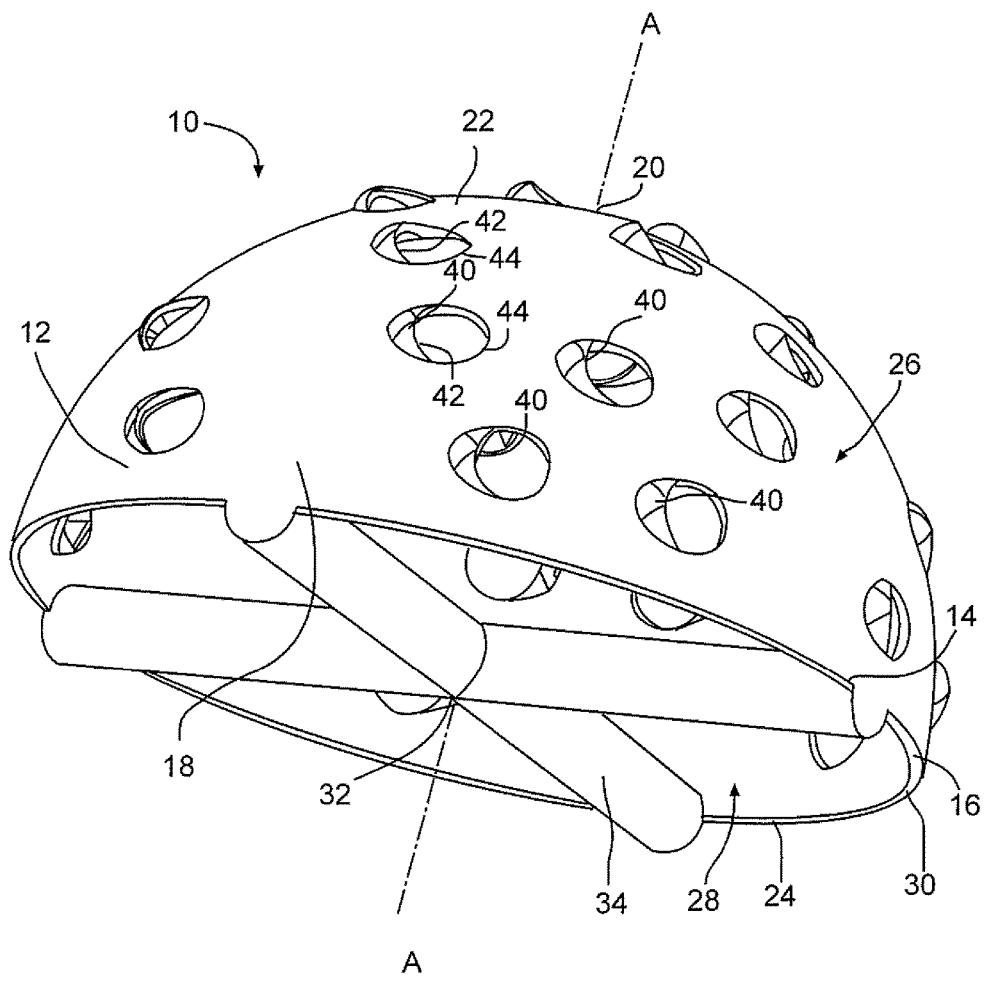
FIG. 1 illustrates a perspective view of an embodiment of a reamer of the present invention.

Now turning to the figures, FIG. 1 illustrates a preferred embodiment of a reamer 10 of the present invention. As illustrated, the reamer 10 preferably comprises a hemispherical cutting shell 12 that extends from an equatorial base 14 at a lower edge 16 of a proximal end 18 to an apex 20 at a distal end 22. The cutting shell 12 is rotatable about a rotational axis A-A that extends through the apex 20. The cutting shell comprises a shell sidewall 24 having an exterior shell surface 26 spaced from a shell interior surface 28 that defines a shell thickness 30 therebetween. A reamer driver interface 32 comprising at least one strut 34, preferably two struts 34 in a cross bar configuration, a bar and boss 36 (FIG. 4), or a ring-and-strut combination (not shown), may be positioned spanning the diameter of the reamer base 14 at the reamer proximal end 18.

The reamer 10 is preferably sized to allow access to tissue in and around the acetabulum. Alternatively, the reamer 10 can also be sized and dimensioned to allow access to other tissue areas. In a preferred embodiment, the wall thickness 30 ranges from about 0.5 mm to about 2 mm. In a preferred embodiment, the shell 12 has an annular perimeter at the lower edge 16 having a diameter from about 20 mm to about 80 mm. The shell 12 also has a shell height 38 (FIG. 2) that extends from the lower edge 16 to the apex 20. It is preferred that the height 38 ranges from about 10 mm to about 50 mm.

In a preferred embodiment, the cutting shell 12 of the reamer 10 of the present invention may be composed of a first material 41 which may include, but is not limited to, various metals, metallic alloys or other materials that are thermally conductive. Examples of first materials may include, but are not limited to, stainless steel (16 $W \cdot m^{-1} \cdot K^{-1}$), MP35N (11 $W \cdot m^{-1} \cdot K^{-1}$), titanium (22 $W \cdot m^{-1} \cdot K^{-1}$), or other biocompatible metals and alloys. In a preferred embodiment, the first material 41 may have a coefficient of thermal conductivity greater than 16 $W \cdot m^{-1} \cdot K^{-1}$.

In an embodiment, a plurality of spaced apart teeth 40 are positioned about the shell 12 extending outwardly from the exterior shell surface 26. In a preferred embodiment, a tissue cutting surface 42 is provided along a portion of an opening 44 that extends through the thickness 30 of the shell 12. In an embodiment, as illustrated in FIG. 1, each of the tissue cutting surfaces 42 is an extension of the shell wall 24 that extends at least partially over the opening 44. In a preferred embodiment, the tissue cutting surfaces 42 are oriented such that they outwardly extend from the exterior wall surface 26 of the shell 12. In an embodiment, the reamer teeth 40 may be constructed with a bent orientation, extending away from the exterior surface 26 of the shell 12 so that they do not lie in the same hemispherical curvature plane of the shell 12. Bending the reamer teeth 40 outwards, as shown in the preferred embodiment of FIG. 1, enables the reamer teeth 40 to "bite" into the tissue, creating a reamed cavity with a smooth surface. This smooth surface is desirable because it allows for a secure implant fit. A smooth reamed surface also reduces physical wear of an implant (not shown) which increases the implant's service life and reduces the need for additional implant replacement surgeries. Specific examples of various teeth and cutting surfaces that may be incorporated with the reamer of the present invention are disclosed in U.S. Pat. Nos. 7,850,691, 8,784,422, and 9,351,740, all to Lechot et al. and U.S. Pat. No. 8,435,243 to White et al., all of which are assigned to the assignee of the present invention and incorporated herein by reference.

Figure 2:
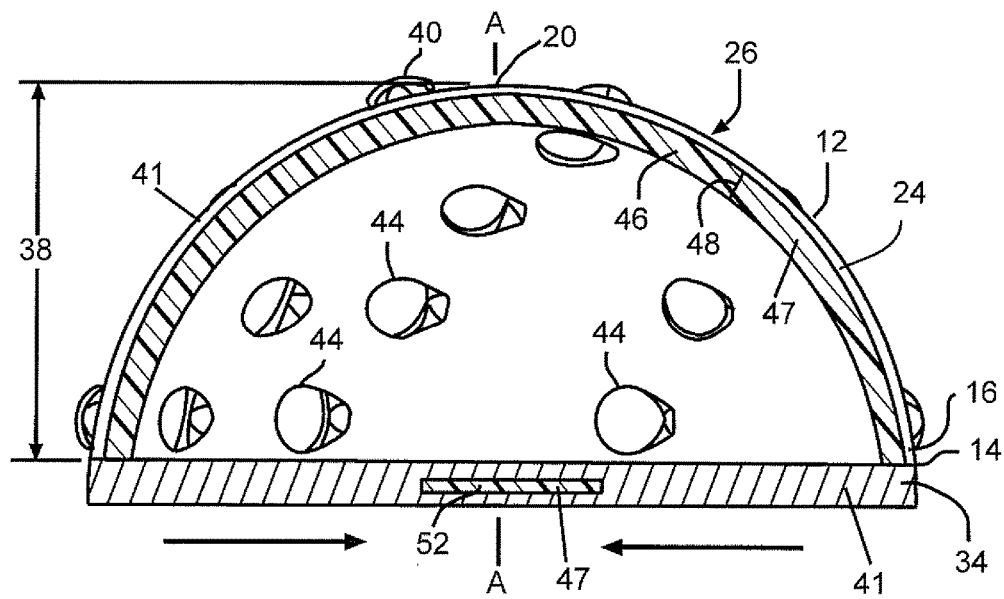
FIG. 2 is a cross-sectional view of an embodiment of a reamer comprising a layer of a second thermally conductive material applied to the interior shell surface.

FIG. 2 illustrates a preferred embodiment in which a layer or coating 46 of a second material 47 having an increased coefficient of thermally conductivity, preferably greater than the coefficient of thermal conductivity of the first material 41 of the shell 12, is applied to the interior surface 28 of the cutting shell 12. This layer 46 of second material 47 having an increased thermal conductivity acts as a heat sink to remove heat from the teeth 40 and tissue cutting surfaces 42 located on the exterior side of the reamer 10. In a preferred embodiment, the layer 46 of second material is applied evenly to the interior shell surface 28. Furthermore, while it is preferred that the layer 46 of second material 47 is applied to the entire interior surface 28, the material may be applied to a portion of the interior surface area of the cutting shell 12. In a preferred embodiment, the layer 46 of second material may be applied to at least ten percent of the interior surface area of the shell 12.

It is contemplated that the layer 46 of second material may be applied to the exterior surface 26 or both interior and exterior surfaces 26, 28 of the cutting shell 12. In an embodiment, the layer 46 of second material 47 is applied to at least a portion of the exterior surface area of the cutting shell 12. In a preferred embodiment, the second material 47 may be applied to the cutting surfaces 42 of the teeth 40. Thus, by applying the second material directly to the tissue cutting surface 42, heat is more efficiently removed from the cutting site. It is preferred that the layer 46 of second material may be applied to at least ten percent of the exterior surface area of the shell 12. Furthermore, multiple second materials may be applied to either or both of the interior or exterior shell surfaces 28, 26. For example graphene may be applied to at least a portion of the exterior shell surface 26 and carbon fiber may be applied to at least a portion of the interior shell surface 28.

In addition to removing heat from the cutting surface 42, application of a thermally conductive material, such as graphene, to the exterior surface 26 of the shell 12 may also reduce friction and increase corrosion and wear resistance. Layer thicknesses 48 of the second material on either of the interior or exterior shell surfaces 28, 26 may preferably range from 0.5 nm to about 100 nm in the case of graphene or between about 0.5 μm to about 5 μm for other second materials having an increased thermal conductivity. In a preferred embodiment, the plurality of tooth openings 44 each extends through the material layer 46 thereby providing a passageway for debris from the reaming process to pass through to collect in the interior of the shell 12.

Preferred second materials have a coefficient of thermal conductivity that is greater than 16 $W \cdot m^{-1} \cdot K^{-1}$. Examples of second materials include, but are not limited to, aluminum (205 $W \cdot m^{-1} \cdot K^{-1}$), gold (310 $W \cdot m^{-1} \cdot K^{-1}$), platinum (70 $W \cdot m^{-1} \cdot K^{-1}$), silver 429 ($W \cdot m^{-1} \cdot K^{-1}$), titanium (22 $W \cdot m^{-1} \cdot K^{-1}$), as well as other carbon materials such as graphite (25-470 $W \cdot m^{-1} \cdot K^{-1}$), carbon fiber (21-180 $W \cdot m^{-1} \cdot K^{-1}$), and diamond 2,500 ($W \cdot m^{-1} \cdot K^{-1}$). A most preferred second material is graphene which has a coefficient of thermal conductivity that ranges from about 3,000 to 5,000 $W \cdot m^{-1} \cdot K^{-1}$. The increased coefficient of thermal conductivity makes graphene an ideal material to act as a heat sink to remove heat from the tissue cutting surfaces 42 of the reamer shell 12. Graphene is an allotrope of carbon and comprises a two-dimensional honey-comb lattice of carbon atoms having a one-atomic thickness. Single layers of graphene have a thickness on the order of about 0.5 nm.

In a preferred embodiment, 1-5 layers of graphene may be applied to either or both of the interior or exterior surfaces 28, 26 of the reamer shell 12. It is contemplated that multiple layers of up to 100 may be applied to the surface 26, 28 of the cutting shell 12 to ensure adequate coverage of the surface and increase durability and corrosion resistance.

The graphene material may be applied to either of the surfaces 26, 28 of the reamer shell 12 using a variety of non-limiting processes. In a preferred embodiment, the thermally conductive material may be applied as a layer or as a coating via chemical vapor deposition, low temperature plasma assisted chemical vapor deposition, sputtering, electrophoretic deposition, or physical vapor deposition process. In a preferred embodiment, methane, acetylene or solid carbon may be used as the carbon source for the chemical vapor deposition process.

Figure 3:
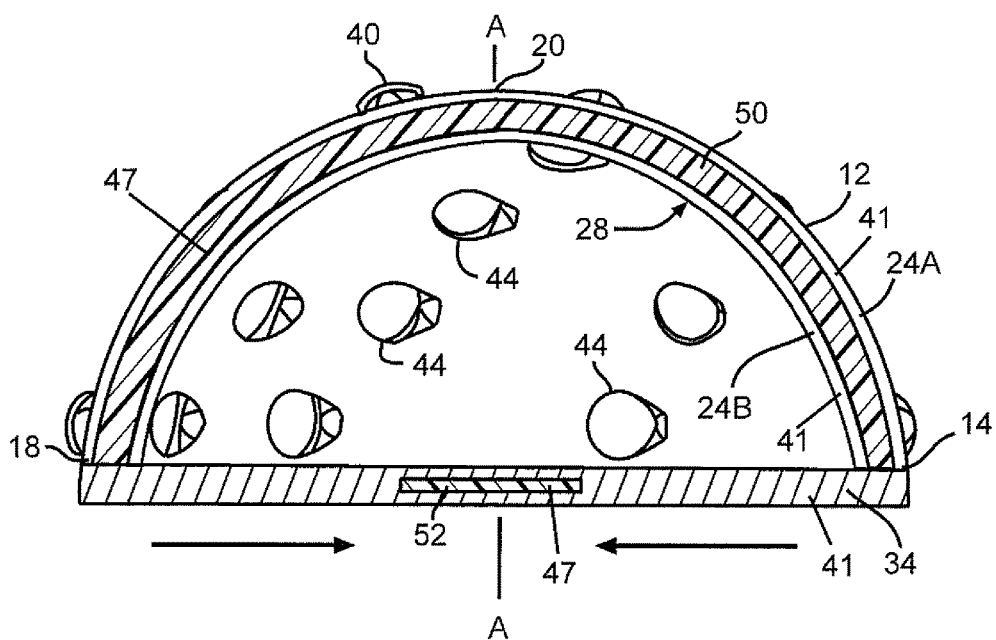
FIG. 3 illustrates a cross-sectional view of an alternative embodiment of a reamer comprising a layer of a second thermally conductive material incorporated within the shell wall.

FIG. 3 illustrates an alternate embodiment in which a layer 50 of the thermally conductive second material 47 may be incorporated within the thickness 30 of the shell wall 24. As shown, the layer 50 of the thermally conductive second material 47 is incorporated within the thickness 30 of the shell wall 24. Encasing the second material 47 within the sidewall thickness 30, as illustrated between exterior and interior sidewall portions 24A and 24B, positions the thermally conductive material closer to the tissue cutting surfaces 42 as compared to applying the second material 47 to the interior shell surface 28, thereby improving heat removal. In a preferred embodiment, the layer 50 of second material 47 that is incorporated within the shell wall 24 may range in thickness from about 0.1 cm to about 0.5 cm. Furthermore, since the second material is encased within the shell thickness 30, heat absorbed by the material layer 50 is efficiently removed by the interior sidewall portion 24B that is in physical contact with the material layer 50.

Figure 4:
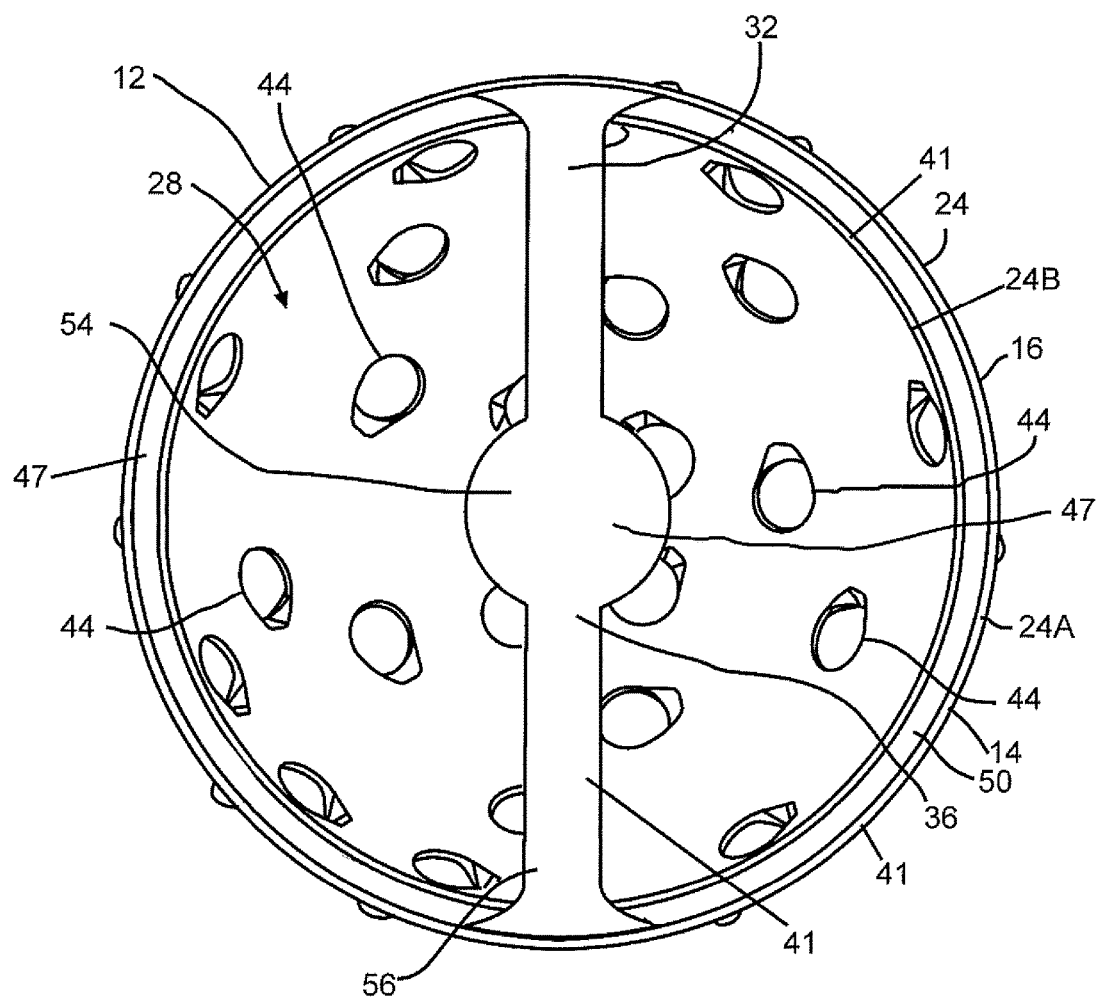
FIG. 4 shows a side view of an alternate embodiment of a reamer comprising a bar and boss driver interface.

FIG. 4 illustrates an embodiment in which the driver interface 32 may be at least partially constructed with the second material 47 or combination of second materials having an increased coefficient of thermal conductivity. As illustrated, the reamer 10 is constructed with a bar and boss driver interface 36 in which at least a portion of the interface structure is constructed with the second material 47. As illustrated, the bar and boss interface 36 has a boss portion 54 that is constructed with the second material 47 while the bar portion is composed of the first material 41. Alternatively, the bar portion 56 may be composed of the second material 47 and the boss portion 54 with the first material 41. In either case, heat that is removed from the tissue cutting surfaces 42 by the layer or layers 46, 50 of thermally conductive second material 47 is conducted to the driver interface 32 where it is removed from the reamer 10.

In an embodiment, the driver interface 32 may also be constructed with the second material 47 incorporated within the structure of the driver interface 32. FIGS. 2 and 3 illustrate an alternate embodiment in which a layer 52 of the second material 47 having an increased coefficient of thermal conductivity is incorporated within at least one strut 34 of the driver interface 32. In a preferred embodiment, this layer 52 of thermally conductive material acts as a heat sink that directs heat away from the reamer shell 12 and towards the driver interface 32 where it exits the reamer 10.

It is further contemplated that the reamer 10 of the present invention may be constructed of multiple second materials such that a gradient of thermal conductivity is created. For example, second materials 47 having different coefficients of thermal conductivity may be applied to the exterior shell surface 26, interior shell surface 28 or incorporated within the shell sidewall 24 and driver interface 32 to create a gradient of increasing coefficient of thermal conductivities throughout the structure of the reamer 10. Such a gradient of thermal conductivities would help encourage heat removal from the tissue cutting surfaces 42.

It is noted that the illustrated embodiments are non-limiting. It is contemplated that these embodiments, or portions thereof, may be combined to form reamers having customized thermal conductivity properties. In addition, different second materials may be incorporated throughout the structure of the reamer 10 to create a customized thermal conductivity profile. This would be of particular benefit as there are a variety of different reamers of different shapes and sizes that are subjected to different mechanical stresses such that different amounts of heat are generated during use. Therefore, the material structure of the reamer 10 can be customized to suit the specific heat profile that is generated during use of the reamer. Furthermore, while it is preferred to incorporate a second material having a greater coefficient of thermal conductivity in a shell composed of a first material having a lower coefficient of thermal conductivity, one may also construct a reamer in which the shell 12 is composed of a second material and a layer of first material is applied to the interior or exterior shell surface or incorporated within the shell sidewall.

Thus, it has been shown that the reamer 10 of the present invention provides for more efficient heat removal. The features of the present invention, such as the layer of thermally conductive material, such as graphene, that is applied to the interior or exterior shell surface 28, 26, positioned within the thickness of the shell 12, or incorporated within the driver interface 32 provides a reamer 10 that efficiently removes heat from the cutting surface 42. Thus, the possibility of bone or tissue necrosis and premature wear of the cutting teeth caused by an increased amount of heat during use is minimized.

It is appreciated that various modifications to the inventive concepts described herein may be apparent to those of ordinary skill in the art without departing from the spirit and scope of the present invention as defined by the appended claims.

What is claimed is:

1. A reamer, which comprises:
   a) a cutting shell having a shell wall with spaced apart exterior and interior shell surfaces, a shell wall thickness therebetween, the shell having a curvature comprising at least a portion of a first hemisphere extending from an apex to a lower edge, the cutting shell being rotatable about a rotational axis that extends through the apex, wherein the cutting shell is composed of a first material having a first coefficient of thermal conductivity;
   b) a second material having a second coefficient of thermal conductivity that is greater than the first coefficient of thermal conductivity of the first material and that contacts at least a portion of the shell interior surface; and
   c) a plurality of cutting teeth, each having a tissue cutting surface, wherein the tissue cutting surface extends outwardly from the exterior surface of the shell.

2. The reamer of claim 1 wherein the first and second materials comprise a metal or metallic alloy.

3. The reamer of claim 1 wherein the second material is selected from the group consisting of graphene, graphite, carbon, gold, titanium, aluminum and combinations thereof.

4. The reamer of claim 1 wherein the second material has a coefficient of thermal conductivity that is greater than 16 $W \cdot m^{-1} \cdot K^{-1}$.

5. The reamer of claim 1 wherein the first material is selected from the group consisting of stainless steel, MP35N, titanium, and combinations thereof.

6. The reamer of claim 1 wherein the second material has a thickness that ranges from about 0.5 nm to about 5 µm.

7. The reamer of claim 1 wherein a driver interface is connected to the reamer shell, and wherein the driver interface is composed of the first material, the second material, or combinations thereof.

8. The reamer of claim 1 wherein an opening that extends through the shell wall and the first and second materials precedes each tissue cutting surface.

9. The reamer of claim 1 wherein the second material contacts the tissue cutting surfaces of the teeth.

10. The reamer of claim 1 wherein the second material is graphene having a coefficient of thermal conductivity from 3,000 to 5,000 $W \cdot m^{-1} \cdot K^{-1}$.

11. The reamer of claim 10 where the graphene is present at a layer thickness of 0.5 nm to 100 nm.

12. The reamer of claim 11 wherein 1-100 layers of graphene are present.

13. A reamer, which comprises:
a) a cutting shell having a shell wall with spaced apart exterior and interior sidewall portions, a sidewall thickness therebetween, the shell having a curvature comprising at least a portion of a first hemisphere extending from an apex to a lower edge, the cutting shell being rotatable about a rotational axis that extends through the apex, the cutting shell exterior and interior sidewall portions composed of a first material having a first coefficient of thermal conductivity and the sidewall thickness at least partially composed of a second material having a second coefficient of thermal conductivity that is greater than the first coefficient of thermal conductivity of the first material; and
b) a plurality of cutting teeth, each having a tissue cutting surface, wherein the tissue cutting surface extends outwardly from the exterior surface of the shell.

14. The reamer of claim 13 wherein the first and second materials comprise a metal or metallic alloy.

15. The reamer of claim 13 wherein the second material is selected from the group consisting of graphene, graphite, carbon, gold, titanium, aluminum and combinations thereof.

16. The reamer of claim 13 wherein the second material has a coefficient of thermal conductivity that is greater than 16 $W \cdot m^{-1} \cdot K^{-1}$.

17. The reamer of claim 13 wherein the first material is selected from the group consisting of stainless steel, MP35N, titanium, and combinations thereof.

18. The reamer of claim 13 wherein a driver interface is connected to the reamer shell, and wherein the driver interface is composed of the first material, the second material, or combinations thereof.

* * * * *